United States Patent [19]
Masuda

[11] Patent Number: 5,680,196
[45] Date of Patent: Oct. 21, 1997

[54] POSITION DETECTING APPARATUS FOR AN OPHTHALMOLOGIC APPARATUS

[75] Inventor: Takashi Masuda, Yamato, Japan

[73] Assignee: Canon Kabushiki Kaisha, Tokyo, Japan

[21] Appl. No.: 493,292

[22] Filed: Jun. 21, 1995

[30] Foreign Application Priority Data

Jun. 23, 1994 [JP] Japan .................. 6-164504

[51] Int. Cl.$^6$ .................. A61B 3/14; A61B 3/10
[52] U.S. Cl. .................. 351/208; 351/211
[58] Field of Search .................. 351/205, 206, 351/208, 210, 212, 214, 211; 354/62

[56] References Cited

U.S. PATENT DOCUMENTS

| | | | |
|---|---|---|---|
| 4,253,743 | 3/1981 | Matsumura | 351/208 |
| 4,660,946 | 4/1987 | Nakamura et al. | 351/212 |
| 4,666,269 | 5/1987 | Nakamura et al. | 351/212 |
| 4,704,012 | 11/1987 | Kohayakawa et al. | 359/462 |
| 4,710,003 | 12/1987 | Masuda et al. | 351/212 |
| 4,755,041 | 7/1988 | Ishikawa et al. | 351/211 |
| 4,764,006 | 8/1988 | Hamano et al. | 351/211 |
| 4,894,670 | 1/1990 | Masuda | 351/214 |
| 5,033,841 | 7/1991 | Nishio et al. | 351/212 |
| 5,056,522 | 10/1991 | Matsumura et al. | 128/645 |
| 5,302,979 | 4/1994 | Maeda et al. | 351/212 |
| 5,365,286 | 11/1994 | Masuda | 351/204 |
| 5,502,521 | 3/1996 | Katou | 351/208 |

*Primary Examiner*—Huy Mai
*Attorney, Agent, or Firm*—Fitzpatrick, Cella, Harper & Scinto

[57] ABSTRACT

A position detecting apparatus for an ophthalmologic apparatus has an image pickup element, a light source, a first projection system for projecting a light beam from the light source onto the cornea of an eye to be examined, a second projection system for projecting one corneal reflection image of the light source onto a plurality of positions on the image pickup element, and a calculator for calculating the central positions of and the distance between the corneal reflection images projected onto the plurality of positions on the image pickup element. The positional deviation of the ophthalmologic apparatus relative to the eye to be examined from an aligned state is quantitatively detected by the calculation by the calculator.

16 Claims, 4 Drawing Sheets

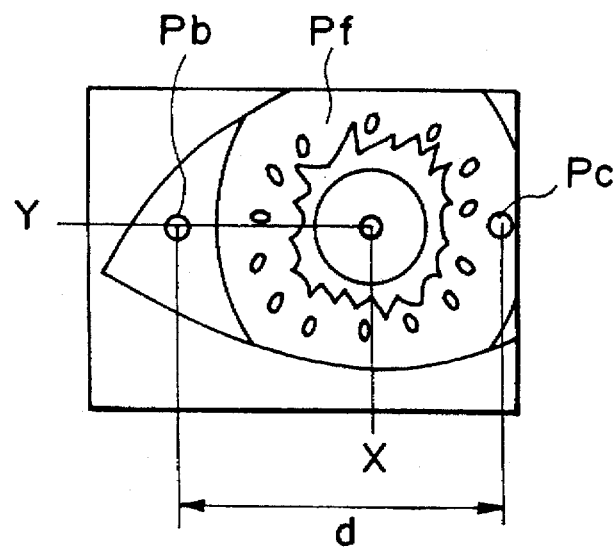
$X \neq X0, Y \neq Y0, d = d0$
F I G. 5
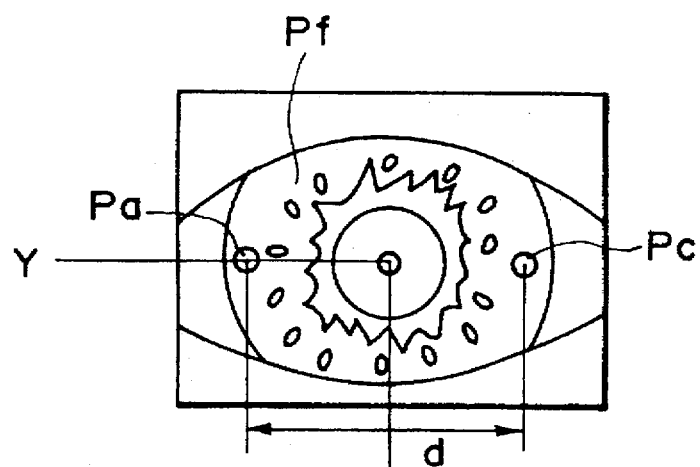
$X = X0, Y = Y0, d \neq d0$
F I G. 6

POSITION DETECTING APPARATUS FOR AN OPHTHALMOLOGIC APPARATUS

BACKGROUND OF THE INVENTION

1. Field of the Invention

This invention relates to a position detecting apparatus for an ophthalmologic apparatus for detecting the aligned state thereof with an eye to be examined.

2. Related Background Art

In an ophthalmologic apparatus such as an ophthalmotonometer, the apparatus body is moved back and forth and the apparatus body is moved vertically and horizontally relative to an eye to be examined to thereby effect the alignment of the eye to be examined and the apparatus body. In order to detect this aligned state, there are known a pair of alignment mark projecting optical systems for projecting a pair of projection light beams toward the cornea of the eye to be examined, and a position detecting apparatus for detecting the coincidence and non-coincidence between the mirror surface reflection images of those light beams by the cornea.

SUMMARY OF THE INVENTION

It is an object of the present invention to provide a position detecting apparatus for an ophthalmologic apparatus capable of simply and quantitatively detecting the relative positional relation between the apparatus and an eye to be examined.

Other objects of the present invention will become apparent from the following detailed description of some embodiments of the invention.

BRIEF DESCRIPTION OF THE DRAWINGS

FIG. 5 is an illustration of images on the image pickup element when alignment is not completed.

FIG. 6 is an illustration of images on the image pickup element when alignment in the direction of a working distance is not completed.

DESCRIPTION OF THE PREFERRED EMBODIMENTS

Figure 1:
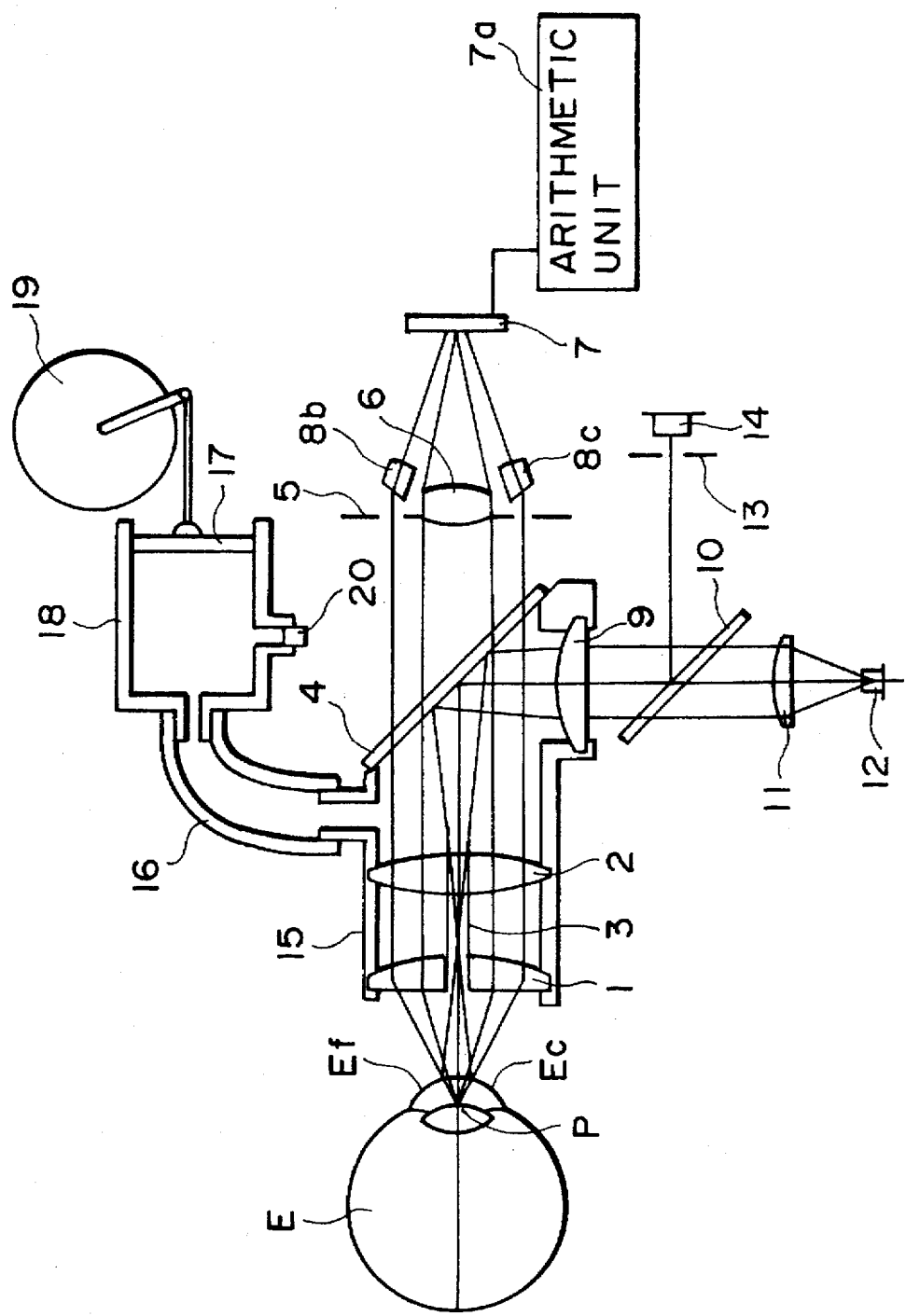
FIG. 1 shows the construction of a first embodiment of the present invention applied to a non-contact ophthalmotonometer.

The present invention will hereinafter be described in detail with respect to some embodiments thereof shown in the drawings.

Figure 2:
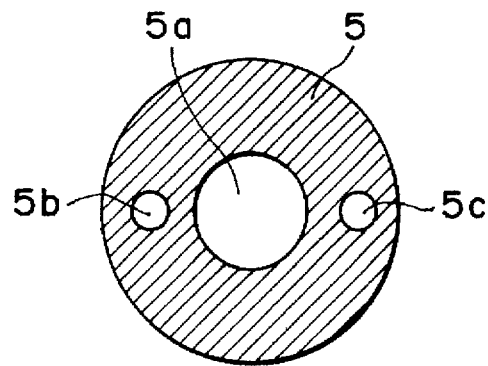
FIG. 2 is a front view of a stop having a plurality of openings.

FIG. 1 shows the construction of a first embodiment of the present invention when it is applied to a non-contact type ophthalmotonometer. Forwardly of an eye E to be examined, there are disposed in succession a nozzle 3 supported by objective lens units 1, 2, a half mirror 4, a plural-aperture stop 5 having openings 5b and 5c disposed symmetrically with respect to a central opening 5a as shown in FIG. 2, a lens 6 and an image pickup element 7. Also, lenses 8b and 8c are disposed on the opposite sides of the lens 6 correspondingly to the openings 5b and 5c in the stop 5.

Figure 3:
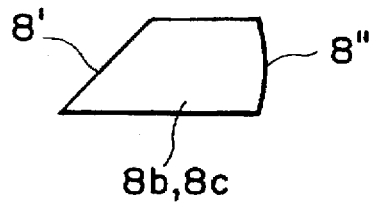
FIG. 3 is a side view of a lens.

A relay lens 9, a half mirror 10, a projection lens 11 and a light source 12 are disposed in succession on the entrance side of the half mirror 4, and an opening 13 and a photo-detector 14 are disposed on the reflection side of the half mirror 10. FIG. 3 shows the lenses 8b, 8c, each of which is comprised of an obliquely disposed surface 8' and a spherical surface 8" and deflects and refracts a light beam so as to form a corneal reflection image P at a predetermined position on the image pickup element 7.

A cylinder 18 having a piston 17 is connected to an air-tight chamber 15 surrounded by the objective lens units 1, 2, the half mirror 4 and the relay lens 9, through tubes 16, and the piston 17 may be driven by a rotary solenoid 19. A pressure sensor 20 is provided in the cylinder 18.

The anterior part of the eye E to be examined is imaged on the image pickup element 7 by the objective lens units 1, 2 and the lens 6. Also, a light beam emitted from the light source 12 is transmitted through the projection lens 11 and the half mirror 10, passes through the interior of the nozzle 3 with the aid of the relay lens 9 and illuminates the cornea Ec of the eye E to be examined. A virtual image P formed by the light beam being reflected by the cornea Ec is refracted by the objective lens units 1, 2, is transmitted through the half mirror 4 and has its light beam separated by the plural-aperture stop 5. The pair of lenses 8b and 8c corresponding to the openings 5b and 5c in the plural-aperture stop 5 form the corneal reflection image P at a predetermined position on the image pickup element 7.

Figure 4:
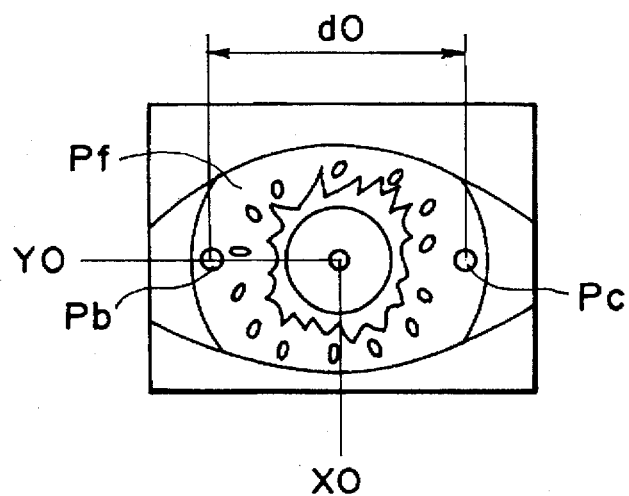
FIG. 4 is an illustration of images on an image pickup element when alignment has been completed.

FIG. 4 shows the images on the image pickup element 7 in the state of FIG. 1, and in the actual apparatus, it corresponds to a monitor-photographed image displayed on a monitor, not shown, contained in the apparatus. An anterior part image Pf has passed through the central opening 5a in the stop 5 and been formed on the element 7 and corneal reflection images Pb and Pc having passed through the marginal openings 5b and 5c are formed are shown in FIG. 4.

The state of FIG. 1 represents a state in which the alignment of the apparatus and the eye E to be examined has been completed and therefore, the intermediate position coordinates X0 and Y0 of the corneal reflection images Pb and Pc in this state and the distance d0 between the two are calculated and memorized. For the detection of the positions of these corneal reflection images, there are widely known a technique of introducing images into a frame memory and extracting them by software, and a technique of comparing video signals from the image pickup element 7 by a comparator and extracting them when a signal of a predetermined level or higher has been obtained.

On the other hand, FIG. 5 shows a state in which the working distance between the eye to be examined and the apparatus is at a predetermined position but alignment in vertical and horizontal directions is not completed. In this case, the distance between the corneal reflection images Pb and Pc is equal to that in the case of FIG. 4, but the central position coordinates X and Y thereof have varied from those in FIG. 4. In this case, the differences (X−X0) and (Y−Y0) of the corneal reflection images Pb and Pc in the state of FIG. 4 from the central position represent an alignment error and therefore, by calculating these, the aligned state can be quantitatively detected. Specifically, these differences (X−X0) and (Y−Y0) are calculated by a calculator 7a.

FIG. 6 shows a state in which alignment in vertical and horizontal directions is completed but the working distance has varied from that in the case of FIG. 4. In this case, the central positions X and Y of the corneal reflection images Pb and Pc are equal to those in FIG. 4, but the distance d therebetween has varied. Again in this case, by calculating the difference (d−d0) in distance from the state of FIG. 4 by the calculator 7a, the error of working distance adjustment can be quantitatively detected.

Thus, by detecting the central positions of the corneal reflection images Pb and Pc and the distance therebetween, the aligned state of the eye E to be examined and the apparatus can be three-dimensionally quantified. When the alignment is terminated, an examiner is informed of it, and the examiner depresses a measuring switch, not shown, or judges that the central positions of the corneal reflection images Pb and Pc and the difference in the distance therebetween have come within predetermined values, and the rotary solenoid 19 is automatically driven to thereby move the piston 17 in the cylinder 18. Air compressed by the piston 17 raises the air pressure in the air-tight chamber 15 through the tubes 16. The pressure-raised air in the air-tight chamber 15 blows out through the nozzle 5 and deforms the cornea Ec of the eye E to be examined.

The light emitted from the light source 12 and reflected by the cornea Ec of the eye E to be examined is transmitted through the opening 13 via the half mirror 4, the relay lens 9 and the half mirror 10 and arrives at the photodetector 14. The opening 13 is disposed at a position conjugate with the corneal reflection image Pc of the light source 12 in a state when the cornea Ec has become flat and therefore, the quantity of light passing through the opening 13 and entering the photodetector 14 becomes a maximum when the cornea Ec is flattened by the compressed air blowing out through the nozzle 5. At this time, a pressure signal from the pressure sensor 20 disposed in the cylinder 18 is converted into an intraocular pressure value.

Figure 7:
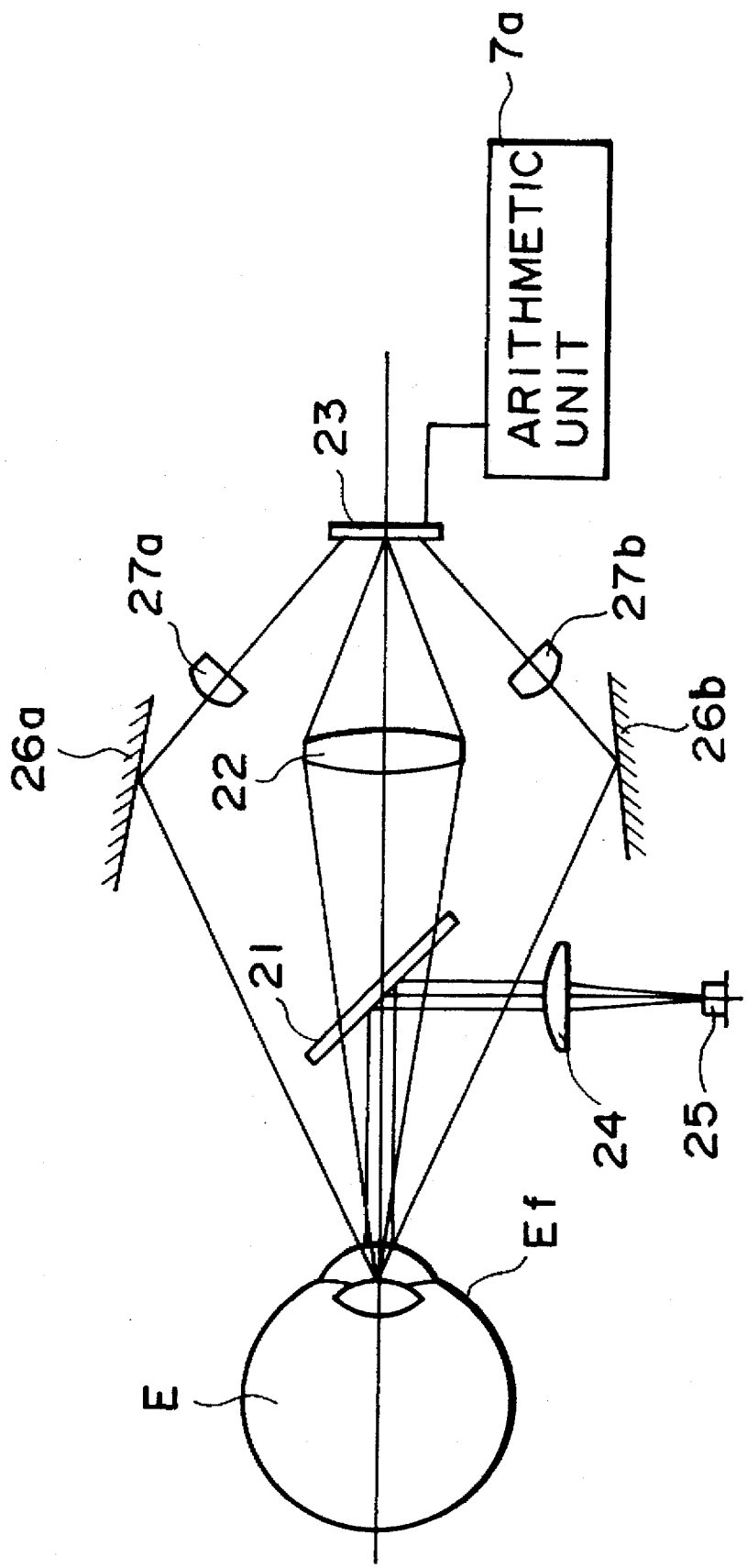
FIG. 7 shows the construction of a second embodiment of the present invention.

Referring now to FIG. 7 which shows the construction of an ophthalmologic apparatus according to a second embodiment of the present invention, a half mirror 21, an observation lens 22 and an image pickup element 23 are arranged forwardly of the eye E to be examined, and a projection lens 24 and a light source 25 are provided in the incidence direction of the half mirror 21. Also, mirrors 26a and 26b are disposed on the opposite sides of the observation lens 22, and lenses 27a and 27b are interposed between the mirrors 26a, 26b and the image pickup element 23.

A light beam emitted from the light source 25 passes through the projection lens 24, is reflected by the half mirror 21 and is projected onto the cornea Ec of the eye E to be examined. Also, the reflection image of the light source 25 by the cornea Ec is reflected by the mirrors 26a and 26b and is projected onto the image pickup element 23 by the lenses 27a and 27b. The anterior part Ef of the eye E to be examined is imaged on the same image pickup element 23 through the observation lens 22. In FIG. 7, only the position detecting construction of the position detecting device applied to an ophthalmotonometer, a retinal camera or the like is shown and units for effecting intraocular pressure measurement, eye fundus photographing, etc. are not shown.

Again in the present embodiment, by the aligned state of the apparatus and the eye to be examined, the images as shown in FIGS. 4 to 6 are projected onto the image pickup element 23 and the aligned state can be detected by a method similar to that in the first embodiment.

Further, in an ophthalmic measuring apparatus wherein a light beam is projected onto an eye to be examined and a characteristic of an eye to be examined is measured by the light beam reflected by the eye to be examined, a light source and further a light position detecting element are shared with an element concerned in measurement, whereby it is not necessary to provide them independently for position detection, and this also leads to advantages in cost and assembly.

While in the above-described embodiments, there is shown only the construction in which the examiner effects the alignment of the eye E to be examined and the apparatus, the intermediate position coordinates of and the distance between the two corneal reflection images are compared with the intermediate position coordinates and the distance in a pre-measured alignment completed state, as previously described, whereby the aligned state of the eye E to be examined and the apparatus can be three-dimensionally and quantitatively detected and therefore, it is easy to automatically effect alignment by providing a driving device in the apparatus itself.

Also, the present embodiment has been shown as an example of the application to a non-contact ophthalmotonometer, but the application of the present invention to an ophthalmologic apparatus such as an auto refractometer, an auto keratometer or a retinal camera in which light from a light source is projected onto an eye to be examined is easy.

As described above, the position detecting apparatus for an ophthalmologic instrument according to the above-described embodiments can project a light beam onto the cornea and quantitatively detect the positions of the apparatus and the eye to be examined on the basis of the positions of and the distance between a plurality of obtained corneal reflection images on the image pickup element.

Particularly, it can quantitatively detect the alignment of the apparatus and the eye to be examined on the basis of the positions of and the distance between at least a pair of obtained corneal reflection images on the image pickup element.

Also, it can quantitatively detect the positions of the apparatus and the eye to be examined on the basis of the positions of and the distance between a plurality of corneal reflection images obtained through the observation optical system on the image pickup element.

What is claimed is:

1. A position detecting apparatus for an ophthalmologic apparatus, comprising:
   an image pickup element;
   a light source;
   a first projection system for projecting a light beam from said light source onto a cornea of an eye to be examined;
   a second projection system for changing one corneal reflection image of said light source to a plurality of corneal reflection images to project the plurality of corneal reflection images onto different positions on said image pickup element; and
   calculating means for calculating the intermediate position coordinates of and the distance between the corneal reflection images projected onto the plurality of positions on said image pickup element, a positional deviation of the ophthalmologic apparatus relative to the eye to be examined from an aligned state being quantitatively detected by the calculation by said calculating means.

2. The apparatus of claim 1, wherein said image pickup element is used also for the observation of the anterior part of the eye to be examined.

3. The apparatus of claim 1, wherein said second projection system has at least a pair of openings and light deflecting means corresponding to said openings, and projects said corneal reflection image corresponding to each of said openings onto said image pickup element.

4. The apparatus of claim 1, further comprising a member for measuring a characteristic of the eye to be examined or photographing the eye to be examined by the reflected light of said light beam from the eye to be examined.

5. The apparatus of claim 1, further comprising an observation optical system for imaging the anterior part of the eye to be examined on said image pickup element and wherein said second projection system has at least a pair of openings disposed in said observation optical system and light deflecting means corresponding to said openings, and projects said corneal reflection image corresponding to each of said openings onto said image pickup element.

6. An ophthalmologic apparatus comprising:

ophthalmologic means for measuring a characteristic of an eye to be examined or photographing the eye to be examined;

an image pickup element;

a light source;

a first projection system for projecting a beam of light from said light source onto the cornea of the eye to be examined;

a second projection system for changing one corneal reflection image of said light source to a plurality of corneal reflection images to project the plurality of corneal projection images onto different positions on said image pickup element; and calculating means for calculating the intermediate position coordinates of and the distance between the corneal reflection images projected onto the plurality of positions on said image pickup element, a positional deviation of said ophthalmologic means relative to the eye to be examined from an aligned state being quantitatively detected by the calculation by said calculating means.

7. The apparatus of claim 6, wherein said image pickup element is used also for the observation of the anterior part of the eye to be examined.

8. The apparatus of claim 6, wherein said second projection system has at least a pair of openings and light deflecting means corresponding to said openings, and projects said corneal reflection image corresponding to each of said openings onto said image pickup element.

9. The apparatus of claim 6, further comprising an observation optical system for imaging the anterior part of the eye to be examined on said image pickup element and wherein said second projection system has at least a pair of openings disposed in said observation optical system and light deflecting means corresponding to said openings, and projects said corneal reflection image corresponding to each of said openings onto said image pickup element.

10. The apparatus of claim 6, wherein said ophthalmologic means executes an intraocular pressure measurement of the eye to be examined.

11. An ophthalmotonometer comprising:

a blowing portion for blowing fluid against an eye to be examined;

a deformation detecting portion for optically detecting the deformed state of the eye to be examined;

a pressure sensor for detecting the fluid pressure of said blowing portion, an intraocular pressure measurement of the eye to be examined being executed by the result of the detection by the pressure sensor obtained on the basis of the detection by said deformation detecting portion;

an image pickup element;

a light source;

a first projection system for projecting a light beam from said light source onto the cornea of the eye to be examined;

a second projection system for changing one corneal reflection image of said light source to a plurality of corneal reflection images to project the plurality of corneal reflection images onto different positions on said image pickup element; and calculating means for calculating the intermediate position coordinates of and the distance between the corneal reflection images projected onto the plurality of positions on said image pickup element, a positional deviation of the ophthalmotonometer relative to the eye to be examined from an aligned state being quantitatively detected by the calculation by said calculating means.

12. The apparatus of claim 11, wherein said image pickup element is used also for the observation of the anterior part of the eye to be examined.

13. A position detecting apparatus for an ophthalmologic apparatus, comprising:

an image pickup element;

a light source;

a first projection system for projecting a light beam from said light source onto a cornea of an eye to be examined;

a second projection system for changing one corneal reflection image of said light source to a plurality of corneal reflection images to project the plurality of corneal reflection images onto different positions on said image pickup element; and calculating means for calculating at least a distance between the corneal reflection images projected onto the plurality of positions on said image pickup element, at least a working distance between the ophthalmologic apparatus and the eye to be examined being quantitatively detected by the calculation by said calculating means.

14. An apparatus according to claim 13, wherein said image pickup element is further used for observation for an anterior portion of the eye to be examined.

15. A position detecting apparatus for an ophthalmologic apparatus comprising:

image pickup means having one image pickup surface;

light emitting means having one light emitting position;

first projecting means for projecting a light beam from said light emitting position onto a cornea of an eye to be examined;

second projecting means for changing one corneal reflection image of said emitting position to a plurality of corneal reflection images to project the plurality of corneal reflection images onto different positions on said image pickup surface; and calculating means for at least calculating a distance between said plurality of corneal reflection images projected onto said different positions on said image pickup surface, whereby at least, a working distance between said apparatus and said eye to be examined is quantitatively detected by calculation by the calculating means.

16. An apparatus according to claim 15, wherein said image pickup element is further used for observation for an anterior portion of said eye to be examined.

* * * * *

UNITED STATES PATENT AND TRADEMARK OFFICE
CERTIFICATE OF CORRECTION

PATENT NO. : 5,680,196
DATED : October 21, 1997
INVENTOR(S) : TAKASHI MASUDA

It is certified that error appears in the above-identified patent and that said Letters Patent is hereby corrected as shown below:

<u>COLUMN 6</u>

Line 58, "least," should read --least--.
   Line 60, "the" should read --said--.

Signed and Sealed this

Thirtieth Day of June, 1998

Attest:

BRUCE LEHMAN

*Attesting Officer*       *Commissioner of Patents and Trademarks*